United States Patent
Schmid et al.

(10) Patent No.: US 9,285,116 B2
(45) Date of Patent: Mar. 15, 2016

(54) METHOD AND A SYSTEM FOR CONVERTING CARBON DIOXIDE INTO CHEMICAL STARTING MATERIALS

(75) Inventors: Günter Schmid, Hemhofen (DE); Dan Taroata, Erlangen (DE); Elena Arvanitis, Somerville, NJ (US); Manfred Baldauf, Erlangen (DE); Frank Walachowicz, Berlin (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 268 days.

(21) Appl. No.: 13/825,232

(22) PCT Filed: Sep. 16, 2011

(86) PCT No.: PCT/EP2011/066073
§ 371 (c)(1),
(2), (4) Date: Mar. 20, 2013

(87) PCT Pub. No.: WO2012/038330
PCT Pub. Date: Mar. 29, 2012

(65) Prior Publication Data
US 2013/0178677 A1    Jul. 11, 2013

Related U.S. Application Data

(60) Provisional application No. 61/508,709, filed on Jul. 18, 2011.

(30) Foreign Application Priority Data

Sep. 20, 2010 (DE) .......................... 10 2010 041 033

(51) Int. Cl.
| | | |
|---|---|---|
| *C07C 1/02* | (2006.01) | |
| *C01B 31/30* | (2006.01) | |
| *C01B 31/20* | (2006.01) | |
| *C01B 31/18* | (2006.01) | |
| *F23J 7/00* | (2006.01) | |
| *B01D 53/62* | (2006.01) | |
| *C01B 21/06* | (2006.01) | |
| *C01C 1/02* | (2006.01) | |
| *C07C 29/151* | (2006.01) | |
| *F23B 99/00* | (2006.01) | |
| *F23G 7/06* | (2006.01) | |
| *F25J 3/04* | (2006.01) | |
| *F23J 15/00* | (2006.01) | |
| *F23L 7/00* | (2006.01) | |
| *B01D 53/14* | (2006.01) | |

(52) U.S. Cl.
CPC . *F23J 7/00* (2013.01); *B01D 53/62* (2013.01); *C01B 21/061* (2013.01); *C01B 31/18* (2013.01); *C01C 1/026* (2013.01); *C07C 1/02* (2013.01); *C07C 29/1518* (2013.01); *F23B 99/00* (2013.01); *F23G 7/06* (2013.01); *F23J 15/00* (2013.01); *F23L 7/00* (2013.01); *F25J 3/04533* (2013.01); *F25J 3/04563* (2013.01); *B01D 53/1475* (2013.01); *B01D 2251/302* (2013.01); *B01D 2252/20484* (2013.01); *B01D 2256/20* (2013.01); *B01D 2257/504* (2013.01); *B01D 2258/0283* (2013.01); *C21C 2100/02* (2013.01); *C21C 2100/06* (2013.01); *F23B 2900/00003* (2013.01); *F23J 2215/10* (2013.01); *F23J 2215/50* (2013.01); *Y02C 10/04* (2013.01); *Y02E 20/12* (2013.01); *Y02W 30/54* (2015.05)

(58) Field of Classification Search
CPC .......... C07C 1/02; C01B 31/30; C01B 31/20; C01B 31/18
USPC .......... 585/534, 638; 423/418.2, 437.1, 445 R
See application file for complete search history.

(56) References Cited

U.S. PATENT DOCUMENTS

| | | | |
|---|---|---|---|
| 5,232,793 A | | 8/1993 | Miyauchi et al. |
| 6,370,865 B1 | | 4/2002 | Sasaki et al. |
| 2002/0092288 A1 | | 7/2002 | Sasaki et al. |
| 2006/0129020 A1 | | 6/2006 | Barends |
| 2009/0016948 A1 | * | 1/2009 | Young ............................ 423/414 |
| 2009/0238731 A1 | * | 9/2009 | Liu et al. ...................... 422/178 |
| 2011/0033355 A1 | | 2/2011 | Smith |
| 2011/0113844 A1 | | 5/2011 | Schmid |
| 2013/0196271 A1 | | 8/2013 | Schmid |

FOREIGN PATENT DOCUMENTS

| | | |
|---|---|---|
| CN | 1050338 A | 4/1991 |
| DE | 69907843 | 5/2004 |
| DE | 102008031437 | 1/2010 |
| DE | 102009014026 | 6/2010 |
| DE | 102010041033.0 | 9/2010 |
| DE | 102010041033 | 3/2012 |
| EP | 0418864 | 3/1991 |

(Continued)

OTHER PUBLICATIONS

Office Action dated May 20, 2015 in corresponding European Patent Application No. 11763889.0.

(Continued)

*Primary Examiner* — Thuan D Dang

(74) *Attorney, Agent, or Firm* — Staas & Halsey LLP

(57) ABSTRACT

A method and apparatus convert carbon dioxide into chemical starting materials. Carbon dioxide is isolated from flue gas emitted by a combustion system. An electropositive metal is burned in an atmosphere of isolated carbon dioxide to reduce the carbon dioxide into chemical starting materials.

10 Claims, 5 Drawing Sheets

(56) References Cited

FOREIGN PATENT DOCUMENTS

| | | |
|---|---|---|
| EP | 0993855 A2 | 4/2000 |
| JP | 6-114238 | 4/1994 |
| WO | 2011/019694 | 2/2011 |
| WO | PCT/EP2011/066073 | 9/2011 |

OTHER PUBLICATIONS

U.S. Appl. No. 61/508,709, filed Jul. 18, 2011, Guenter Schmid et al., Siemens AG.

European Office Action mailed Mar. 13, 2014 in corresponding European Application No. 11763889.0.

European Office Action for related European Patent Application No. 11 763 889.0, issued Nov. 12, 2014, 6 pages.

Der-Yan Hwang et al., "Reaction Mechanism of $CO_2$ with Ca atom: A Theoretical Study," Chemical Physics Letters 331, 2000, 7 pages.

F. Ausfelder et al., "Verwertung and SpeicherUng von $CO_2$," Diskussionspapier, Dechema, Oct. 2008, 36 pages, http://www.dechema.de/dechema_media/diskussionco2.pdf.

Dirk Walther, "Chemie mit $CO_2$," Nachricht aus der Chemie, 55, Dec. 2007, 7 pages.

Howard Herzog et al., "Advanced Post-Combustion $CO_2$ Capture," Apr. 2009, 39 pages, http://sequestration.mit.edu/pdf/Advanced_Post_Combustion_CO2_Capture.pdf.

Office Action mailed Feb. 2, 2015 for corresponding Chinese Patent Application No. 201180055809.9.

English language PCT Forms PCT/ISA/220, PCT/ISA/210 and PCT/ISA/237 for PCT/EP2011/066073, mailed Apr. 10, 2013.

* cited by examiner

METHOD AND A SYSTEM FOR CONVERTING CARBON DIOXIDE INTO CHEMICAL STARTING MATERIALS

CROSS REFERENCE TO RELATED APPLICATIONS

This application is based on and hereby claims priority to International Application No. PCT/EP2011/066073 filed on Sep. 16, 2011 and German Application No. 10 2010 041 033.0 filed on Sep. 20, 2010 and U.S. Provisional Application No. 61/508,709 filed on Jul. 18, 2011, the contents of which are hereby incorporated by reference.

BACKGROUND

The invention relates to a method and a system for converting carbon dioxide into chemical feedstocks.

Along with power generation, conventional fossil fuel combustion generates various chemical by-products, such as nitrogen-, carbon- and sulphur oxides which exit the boiler or combustion chamber in the form of flue gas. In the past it was acceptable to allow flue gas to discharge from power plants and industrial facilities directly into the atmosphere without further treatment. However, with increasing evidence about environmental damage linked to, for example, the acidification of the atmosphere as a result of sulfur oxide emissions and the risk of adverse climate change from global warming due to greenhouse gas emissions, flue gas treatment to mitigate emissions with pollution abatement techniques is becoming more important. Conventional technologies for flue gas treatment involve resource and energy intensive processes which increase considerably operating costs. Carbon capture technologies focus on preventing carbon dioxide from entering the atmosphere. In the case of emissions from industrial applications, abatement methods of various maturity levels exist presently to capture carbon dioxide and to recover it as a concentrated stream that is amenable to geological sequestration or as a raw material for industrial processes. Commercial post-combustion carbon dioxide capture systems currently in operation involve carbon dioxide absorption with aqueous monoethanolamine MEA. MEA can be used in aqueous solutions for scrubbing certain acidic gases such carbon dioxide. The process takes place in tall columns known as scrubbers in which a turbulent flow promotes a rapid carbon dioxide transfer from gas to liquid. Differences in density make it easy to separate the emerging gas and liquid. To recover the captured carbon dioxide, the loaded solvent is pumped to a stripper in which it is exposed to hotter carbon dioxide free gas, typically steam. Upon heating, carbon dioxide is desorbed. The stripped liquid is pumped back to the scrubber while the mixture of steam and carbon dioxide is cooled to condense the steam, leaving behind high-purity carbon dioxide suitable for compression and, after transportation to an appropriate site, sequestration as described for example by Howard Herzog, Jerry Meldon, Alan Hatton, Advanced Post Combustion carbon dioxide capture, April 2009 (http://web.mitedu/mitei/docs/reports/herzog-meldon-hatton.pdf). Accordingly, isolating of carbon dioxide from a flue gas and using the isolated carbon dioxide for further processing is known. In a conventional combustion system fuel such as carbon is burned in a burning stage with an exothermic reaction to generate energy and the carbon dioxide forming reaction products of the reaction can be isolated from the flue gas emitted by the combustion system.

However, conventional combustion systems do not use the generated carbon dioxide to produce valuable fine chemical products which could be used as chemical starting materials in further synthetic processes. Conventional post-combustion carbon dioxide capture systems, as used in power plants and in particular coal fired power plants CFPP, focus on isolating carbon dioxide in the flue gas without using the separated carbon dioxide as a chemical compound which could be used in further synthetic processes.

SUMMARY

Accordingly, it is an object of the present invention to provide a combustion method and system for producing chemical starting materials which can be used in further chemical synthetic processes.

The inventors propose a method for converting carbon dioxide into chemical starting materials, wherein the method comprises the steps of:

(a) isolating the carbon dioxide from flue gas emitted by a combustion system; and (b) burning an electropositive metal in an atmosphere of the isolated carbon dioxide to reduce the carbon dioxide into the chemical starting materials.

According to the method carbon dioxide is not only isolated from the flue gas but also used to produce chemical starting materials which can be further processed in a synthetic process.

In a possible embodiment of the proposed method, the electropositive metal is formed by an element of the first, second or third group of the periodic table.

In a possible embodiment of the method, one element of the following group of elements is used for burning in an atmosphere of the isolated carbon dioxide:

Lithium, sodium, potassium in the first group of the periodic table, magnesium, calcium, strontium, barium in the second group of the periodic table, and aluminium and zinc in the third group of the periodic table.

In a possible embodiment of the method a thermal energy provided by the exothermic burning reaction of the electropositive metal with the isolated carbon dioxide is used to power a generator being adapted to produce electricity.

In a possible embodiment of the method the electropositive metal is heated up to provide a molten electropositive metal before burning the molten electropositive metal in the atmosphere of the isolated carbon dioxide.

In a possible preferred embodiment of the method the used electropositive metal comprises lithium.

The use of lithium provides the advantage that lithium has a high electropositivity and other useful characteristics. Lithium is the lightest metal in the periodic table and can even can float when transported on water in a container and even on oil. Furthermore, lithium has a very low density and approximately 0.534 g/cm$^3$ and can be transported because of its low weight easily. The metal is so soft that it can also be cut with a knife. Accordingly, it is easy to process lithium metal mechanically. Furthermore, lithium has 180° C. a relatively low melting point of 180° C.

In a possible embodiment of the method the electropositive metal is heated up to provide a molten electropositive metal before burning the molten electropositive metal in the atmosphere of the isolated carbon dioxide.

In a possible embodiment of the method the chemical starting materials are used in a further synthesis process.

In a possible embodiment of the method the chemical starting material produced by reducing the carbon dioxide comprises carbon monoxide.

The produced carbon monoxide can be converted carbon containing starting materials, in particular methanol.

In a further possible embodiment of the method the chemical starting material produced by reducing the carbon dioxide comprises carbide.

The produced carbide can be further converted into acetylene.

In a possible embodiment of the method the electropositive metal is regenerated from reaction products of the burning reaction of the electropositive metal with the carbon dioxide isolated from the flue gas of the combustion system.

In a possible embodiment of the method the flue gas is isolated from a post-combustion carbon capture system at a coal fired power plant or other industrial combustion processes, e.g. cement plants or steel works.

In a possible embodiment of the method the lithium carbonate is converted by aqueous hydrochloride acid into lithium chloride which is converted by electrolysis into lithium metal forming the electropositive metal being burned in the atmosphere of isolated carbon dioxide.

In a possible embodiment of the method the regenerated lithium metal is transported for reacting with the isolated carbon dioxide as a metal in solid or liquid form or as lithium hydride in solid form.

The inventors further propose a system for converting carbon dioxide into chemical starting materials used for synthetic processes, the system comprising:
  isolating device(s) for isolating the carbon dioxide from flue gas emitted by a combustion apparatus; and
  burning device(s) for burning an electropositive metal in an atmosphere of the isolated carbon dioxide to reduce the carbon dioxide into the chemical starting materials.

The inventors further propose a closed loop conversion system for converting carbon dioxide into chemical starting materials, the closed loop conversion system comprising:
  isolating device(s) adapted to isolate carbon dioxide from flue gas emitted by a combustion apparatus;
  burning device(s) adapted to burn in an exothermic burning reaction an electropositive metal in an atmosphere of the isolated carbon dioxide to reduce the carbon dioxide to the chemical starting materials; and
  regenerating device(s) adapted to regenerate the electropositive metal from reaction products of the exothermic burning reaction.

In a possible embodiment of the closed loop conversion system the regenerating device(s) are adapted to convert the reaction products of the exothermic burning reaction by electrolysis into the electropositive metal.

In a possible embodiment of the closed loop conversion system the regenerated electropositive metal comprises at least an element of the first, second and third group of the periodic system or Zinc, in particular a lithium metal.

The inventors further propose a method for industrial use of a compound, wherein the compound is converted in a burning step by an electropositive metal and wherein at least one burning product of the burning step is converted further in a reaction step.

In a possible embodiment of this method the compound comprises carbon dioxide and/or nitrogen.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
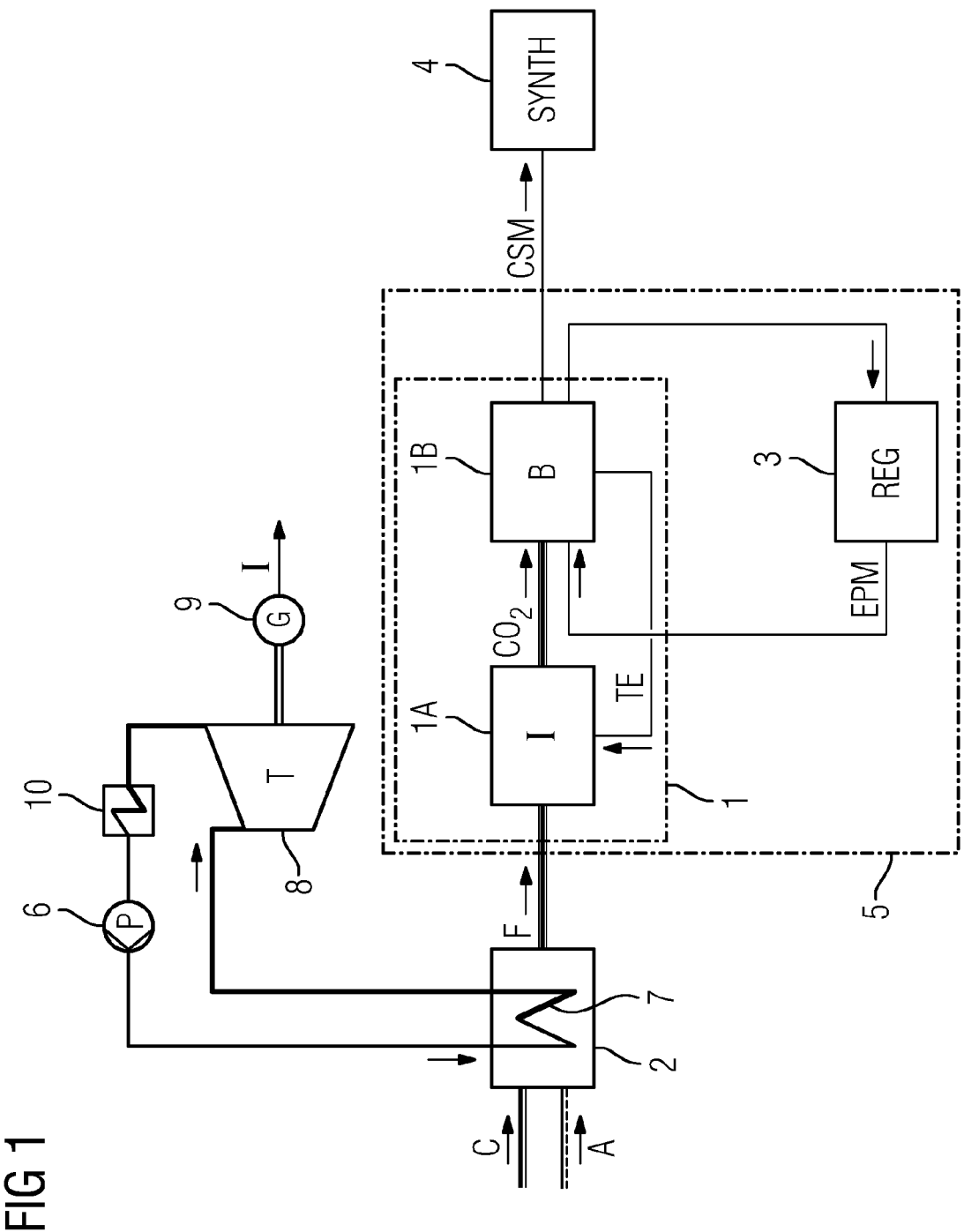
FIG. 1 shows a block diagram of a system for converting carbon dioxide into chemical starting materials used for synthesis processes according to a possible embodiment.

Reference will now be made in detail to the preferred embodiments of the present invention, examples of which are illustrated in the accompanying drawings, wherein like reference numerals refer to like elements throughout.

As can be seen from FIG. 1 a system 1 for converting carbon dioxide $CO_2$ into chemical starting materials CSM used for synthesis processes comprises in a possible embodiment two stages. The system 1 comprises isolating device(s) 1A for isolating the carbon dioxide from flue gas F emitted by a combustion apparatus 2. The isolating device(s) or isolating stage 1A outputs the isolated carbon dioxide $CO_2$ to burning device(s) or a burning stage 1B provided for burning an electropositive metal EPM in an atmosphere of the isolated carbon dioxide $CO_2$ to reduce the carbon dioxide $CO_2$ into chemical starting materials CSM. The electropositive metal EPM comprises in a possible embodiment at least one element of the first, second or third periodic group within the periodic table or Zinc. In a preferred embodiment the electropositive metal EPM is formed by a lithium metal. In the embodiment as shown in FIG. 1 an electropositive metal EPM, such as lithium metal, is regenerated from reaction products of the exothermic burning reaction which takes place in the burning stage 1B of the system 1. The reaction products of the exothermic burning reaction are supplied to regenerating device(s) or a regenerating stage 3 which is adapted to regenerate the electropositive metal EPM from the reaction products supplied to the regenerating stage 3 by the burning stage 1B. As can be seen in FIG. 1 chemical starting products or chemical starting materials CSM formed by the reduction of the carbon dioxide $CO_2$ with the electropositive metal EPM can be supplied to a synthetic processing stage 4.

The system 1 for converting carbon dioxide into the chemical starting materials CSM and the regenerating stage 3 form together a closed loop conversion system 5 as shown in FIG. 1. This closed loop conversion system 5 is also provided for converting carbon dioxide into chemical starting materials CSM and comprises in the shown embodiment three units or entities. The closed loop conversion system 5 comprises the isolating stage 1A adapted to isolate carbon dioxide from flue gas emitted by the combustion apparatus 2, the burning stage 1B being adapted to burn in an exothermic burning reaction the electropositive metal EPM in an atmosphere of the isolated carbon dioxide to reduce the carbon dioxide to chemical starting materials CSM and the regenerating stage 3 adapted to regenerate the electropositive metal EPM from the reaction products of the exothermic burning reaction which takes place in the burning stage 1B. It can be seen in FIG. 1 that the input to the closed loop conversion system 5 is the flue gas F and the output of the closed loop conversion system 5 is formed by the chemical starting material CSM which can be used in a following synthetic chemical process.

The thermal energy TE provided by the exothermic burning reaction of the electropositive metal EPM with the isolated carbon dioxide $CO_2$ can be used to power a generator being adapted to produce electricity. A part of the thermal energy TE provided by the exothermic burning reaction of the electropositive metal EPM with the carbon dioxide $CO_2$ can be fed back from the burning stage 1B to the isolating stage 1A to supply thermal energy to a desorption process of a carbon dioxide capture/isolation process performed in the isolating stage 1A.

The electropositive metal EPM shown in FIG. 1 can be supplied in an alternative embodiment by a separate source providing the electropositive metal. In a possible embodiment the electropositive metal EPM comprises at least one metal or element of the first, second and third periodic group in the periodic table, in particular lithium, sodium, potassium, magnesium, calcium, strontium, barium, aluminium and zinc.

The system 1 in the closed loop conversion system 5 can be integrated in a power plant comprising the combustion apparatus 2. This power plant can be for example a coal fired power plant CFFP. Carbon C as well as air A is supplied to the combustion apparatus 2. Heat generated by the exothermic burning reaction of the supplied carbon C and the oxygen of the air A is used as thermal energy and a heated-up fluid is pumped by a pump 6 to a heat exchanger 7 provided within the combustion chamber of the combustion apparatus 2 as shown in FIG. 1. The heated-up fluid is used in the shown embodiment to drive a turbine 8, such as a steam turbine. The turbine 8 in turn drives an electric generator 9 for producing an electric current I. The heated-up fluid running the turbine 8, such as steam, can then be fed back to the pump 6 via a condenser 10 which can be cooled by water coming from a cooling tower getting its water from a river.

Figure 2:
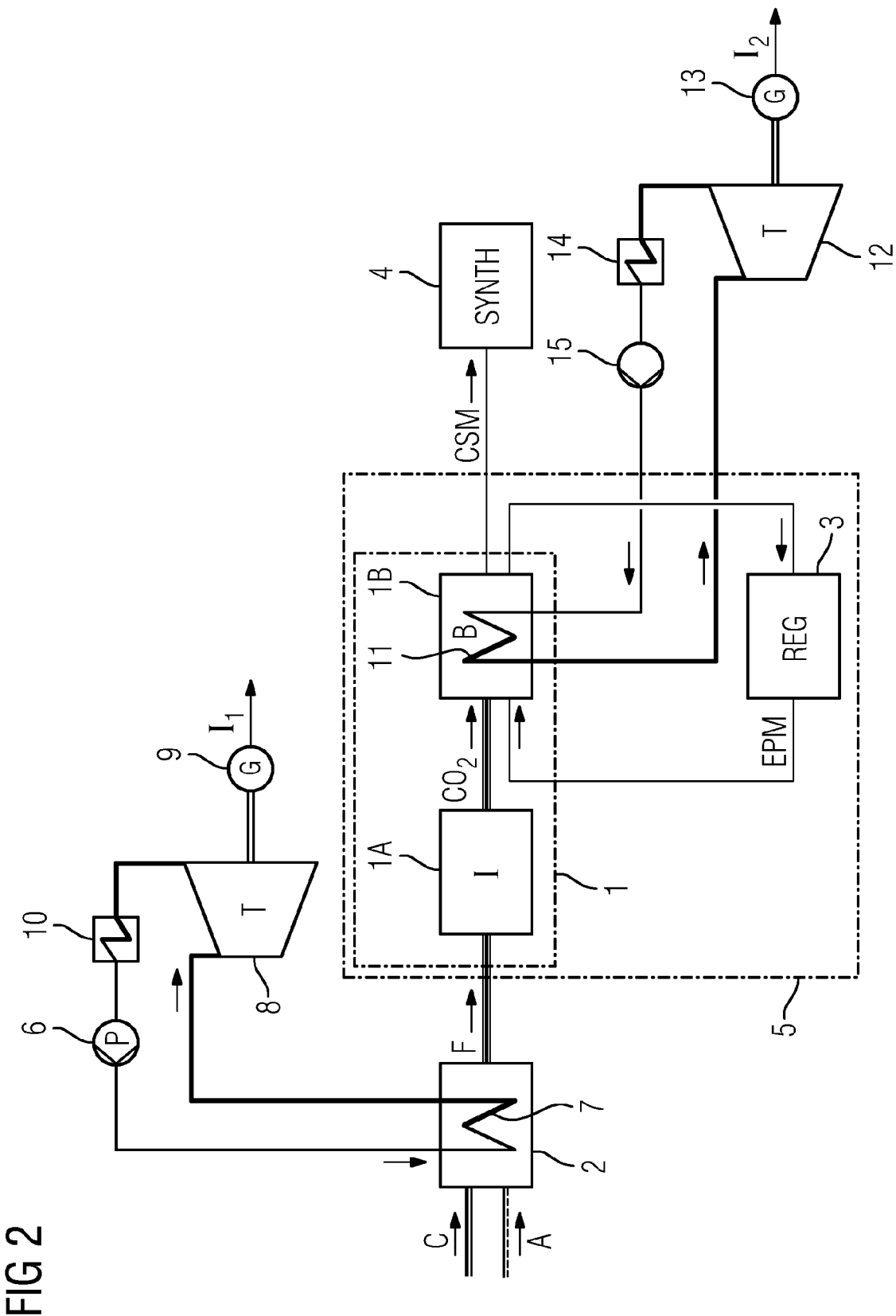
FIG. 2 shows a flow chart of a possible embodiment of a method for converting carbon dioxide into chemical starting materials according to a possible embodiment.

In a possible embodiment of the system 1 for converting carbon dioxide into chemical starting materials as shown in FIG. 2 the burning stage 1B for burning the electropositive metal EPM in an atmosphere of the isolated carbon dioxide comprises a second heat exchanger 11 supplying the heated fluid to a second turbine 12 connected to a further generator 13 and to a second condenser 14 which supplies the cooled fluid via a second pump 15 to the heat exchanger 11 of the burning stage 1B. In the embodiment as shown in FIG. 2 the heat exchanger 11 of the burning stage 1B is provided within a second closed loop driving the second generator 13 by the turbine 12.

In a further embodiment the heat exchanger 7 of the combustion chamber within the combustion apparatus 2 as well the heat exchanger 11 within the burning stage 1B are connected in series to form a closed loop in which a heatable fluid for the turbines 8, 12 circulates.

According to the proposal, the thermal energy provided by the exothermic burning reaction of the electropositive metal EPM with the isolated carbon dioxide can be used to drive at least generators 9, 13 adapted to produce electricity. In the burning stage 1B the strong exothermic reaction of carbon dioxide $CO_2$ with the electropositive metal EPM, in particular lithium, produces a thermal energy that exceeds 1100° C. and which can power the steam turbine 12 and the generator 13 to generate electricity. The thermal energy TE can also be used for a carbon capture system of the isolating stage 1A. Further the thermal energy produced by the burning stage 1B is used in a possible embodiment to heat up the electropositive metal EPM supplied to the burning stage 1B. The produced electricity not only can be added to the total energy output of the power plant but can also be used to power on-site energy intensive processes. In particular, the produced electricity can also be used for synthesis processes taking place in the synthesis stage 4 as shown in FIGS. 1, 2. The thermal energy provided by the reaction between the electropositive metal EPM and carbon dioxide can also be used to power the carbon dioxide isolation or desorption process. The thermal energy from the burning reaction of carbon dioxide $CO_2$ with the electropositive metal EPM can be used in other industrial processes and other applications such as district heating of an area around the power plant. The thermal energy produced by the burning stage 1B can also be stored.

At atmospheric pressure and temperatures exceeding 180° C., i.e. the melting point of lithium, molten lithium can react with isolated carbon dioxide $CO_2$ in the burning stage 1B to provide either lithium oxide $LiO_2$ and carbon monoxide.

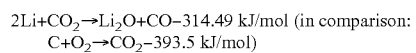

$2Li+CO_2 \rightarrow Li_2O+CO-314.49$ kJ/mol (in comparison: $C+O_2 \rightarrow CO_2-393.5$ kJ/mol)

Further, molten lithium Li can react with carbon dioxide $CO_2$ to form lithium oxide and carbon depending on the reaction's stoechiometry and kinetics vs. thermodynamics:

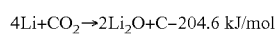

$4Li+CO_2 \rightarrow 2Li_2O+C-204.6$ kJ/mol

Carbon produced in this reaction can in turn react with either excess carbon dioxide $CO_2$ to yield carbon monoxide:

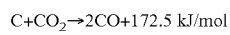

$C+CO_2 \rightarrow 2CO+172.5$ kJ/mol

The generated carbon monoxide CO can further be converted into methanol.

Further, the carbon can react with excess lithium Li to yield lithium carbide:

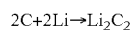

$2C+2Li \rightarrow Li_2C_2$

This lithium carbide $Li_2C_2$ can further be converted into acetylene.

Both carbon monoxide CO as well as lithium carbide $Li_2C_2$ produced by the exothermic reaction in the burning stage 1B form commercially valuable starting materials because they can be converted respectively into chemical commodities such as methanol via the commercial Fischer-Tropsch process and acetylene following aqueous quench. Accordingly, carbon monoxide CO and lithium carbide $Li_2C_2$ form chemical starting materials CSM for a following synthesis processing stage 4 as shown in FIGS. 1, 2. The produced acetylene itself forms an important material for the synthesis of oxygenated olefins via the metal-catalyzed Reppe chemistry and the formation of ethylene for the polymer industry. The resulting lithium oxide $Li_2O$ can also react further with excess carbon dioxide to form lithium carbonate:

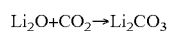

$Li_2O+CO_2 \rightarrow Li_2CO_3$

Lithium carbonate $Li_2CO_3$ can itself decompose at the given temperature back into lithium oxide $Li_2O$ and carbon dioxide:

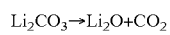

$Li_2CO_3 \rightarrow Li_2O+CO_2$ (at relevant temperatures around 1500° C.)

Further, it is possible that the lithium carbonate $Li_2CO_3$ reacts with carbon, present in the reaction medium, to generate lithium carbide $Li_2C_2$ and carbon monoxide:

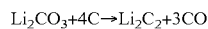

$Li_2CO_3+4C \rightarrow Li_2C_2+3CO$

Heat of formation (298 k): $Li_2O=597$ kJ/mol; $Li_2CO_3=-1215.87$ kJ/mol

Lithium carbonate is the solid reaction product of the carbon dioxide reduction which takes place in the burning stage 1B. Lithium carbonate is a stable and commercially valuable lithium salt that can in turn be converted with aqueous hydrochloric acid (HCl) to lithium chloride, the starting material for the generation of lithium metals by electrolysis.

Accordingly, the power plant as shown in the embodiments of FIGS. 1, 2 is not only provided for generating electrical or thermal energy but also for producing chemical starting materials CSM which can be used in a further synthesis process performed by a synthesis processing stage 4 at the location of the power plant or at a remote synthesis processing stage 4.

In a possible embodiment the used electropositive metal EPM is formed by lithium. By burning the electropositive lithium in the atmosphere of the isolated carbon dioxide can be used based on the reaction's stoechiometry, efficiency, $CO_2$ conversion and ease of product separation.

Lithium can be heated up to temperatures T exceeding its melting point of 180° C. The resultant molten lithium Li can for instance have a temperature T in a range between 200° C. and 600° C. or even more and is then injected into the reaction chamber of the burning stage 1B. In order to increase the reaction surface area and rate pressurized injection of atomized molten lithium in the carbon dioxide gas flow is performed. This can be realized by making use of an injection nozzle as part of the burning stage 1B. The necessary energy for the lithium melting process can also be obtained from the energy generated by burning lithium Li in the carbon dioxide $CO_2$ within the burning or reaction chamber of the burning stage 1B.

In an alternative implementation the reaction between lithium Li and carbon dioxide $CO_2$ is performed as follows. In this alternative implementation, the reaction chamber of the burning stage 1B includes a molten lithium bath or a molten lithium alloy bath, for example at temperatures between 200° C. and 600° C. In this bath the pressurized carbon dioxide gas flow is injected. Two lithium densities of about 0.53 g/cm³ solid reaction products deposit and are collected at the bottom of the chamber whereas gaseous reaction products are collected via an outlet at the top of the cell in the burning stage 1B.

Figure 5:
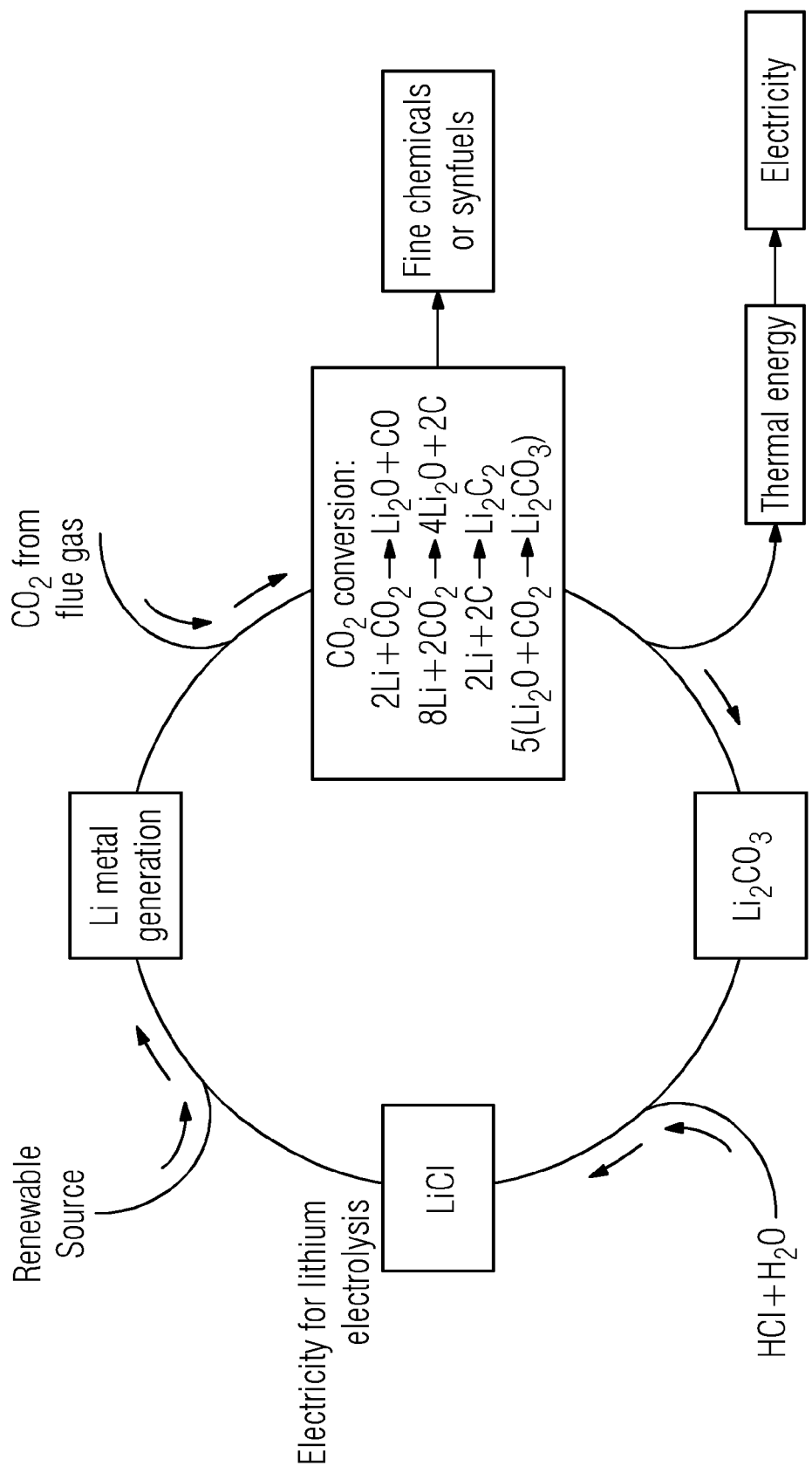
FIG. 5 shows a diagram illustrating the utilization of a lithium cycle to convert carbon dioxide into chemical starting materials and for generating electricity according to a possible embodiment.

The regenerating stage 3 for regenerating the electropositive material used for the exothermic chemical reaction of the burning stage 1B can make use of a closed lithium cycle as illustrated in FIG. 5. In this embodiment the lithium metal Li is regenerated from lithium carbonate $Li_2CO_3$ and lithium oxide $Li_2O$ generated as reaction products of the burning reaction of lithium with carbon dioxide isolated from that gas flue of the combustion system. The lithium carbonate $Li_2CO_3$ can be converted by aqueous hydrochloride acid into lithium chloride which is converted by electrolysis into lithium metal Li forming the electropositive metal EPM being burned in the atmosphere of the isolated carbon dioxide. As shown in the cycle of FIG. 5 the electropositive metal EPM such as lithium Li acts as energy storing medium and as an energy conveyor. Electrical energy from renewable sources can be used for electrolysis of lithium chloride LiCl to lithium metal Li. Further, the lithium Li is used to transfer the energy from renewable sources to a fossil-fuel powered process. The reaction products of the exothermic reaction within the burning stage 1B such as lithium oxide and lithium carbonate are used to regenerate lithium via the lithium chloride intermediate, hence minimizing resource consumption. This is an important attribute of the closed lithium cycle as shown in FIG. 5, especially when future global demand in lithium ion sources is expected to increase as worldwide production of lithium batteries for electronics and automotive applications is expanded.

Figure 3:
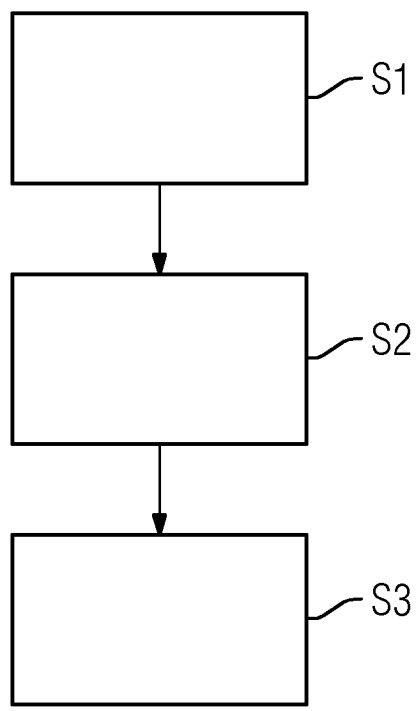
FIG. 3 shows a diagram for illustrating post combustion carbon dioxide capture by reduction of the carbon dioxide with an electropositive metal according to a possible embodiment.

FIG. 3 shows a flow chart of a possible embodiment of a method of converting carbon dioxide $CO_2$ into chemical starting materials CSM.

In a first step S1 the carbon dioxide is isolated from the flue gas emitted by a combustion system or a combustion apparatus such as the combustion apparatus 2 shown in FIGS. 1 and 2.

In a further step S2 an electropositive metal EPM such as lithium Li is burned in an atmosphere of the isolated carbon dioxide $CO_2$ to reduce the carbon dioxide $CO_2$ into chemical starting materials CSM.

In a further step S3 the electropositive metal EPM can be regenerated from the reaction products of the exothermic burning reaction taking place in the burning stage 1B. In a possible implementation the reaction products of the exothermic burning reaction are converted by electrolysis into the electropositive metal EPM.

Figure 4:
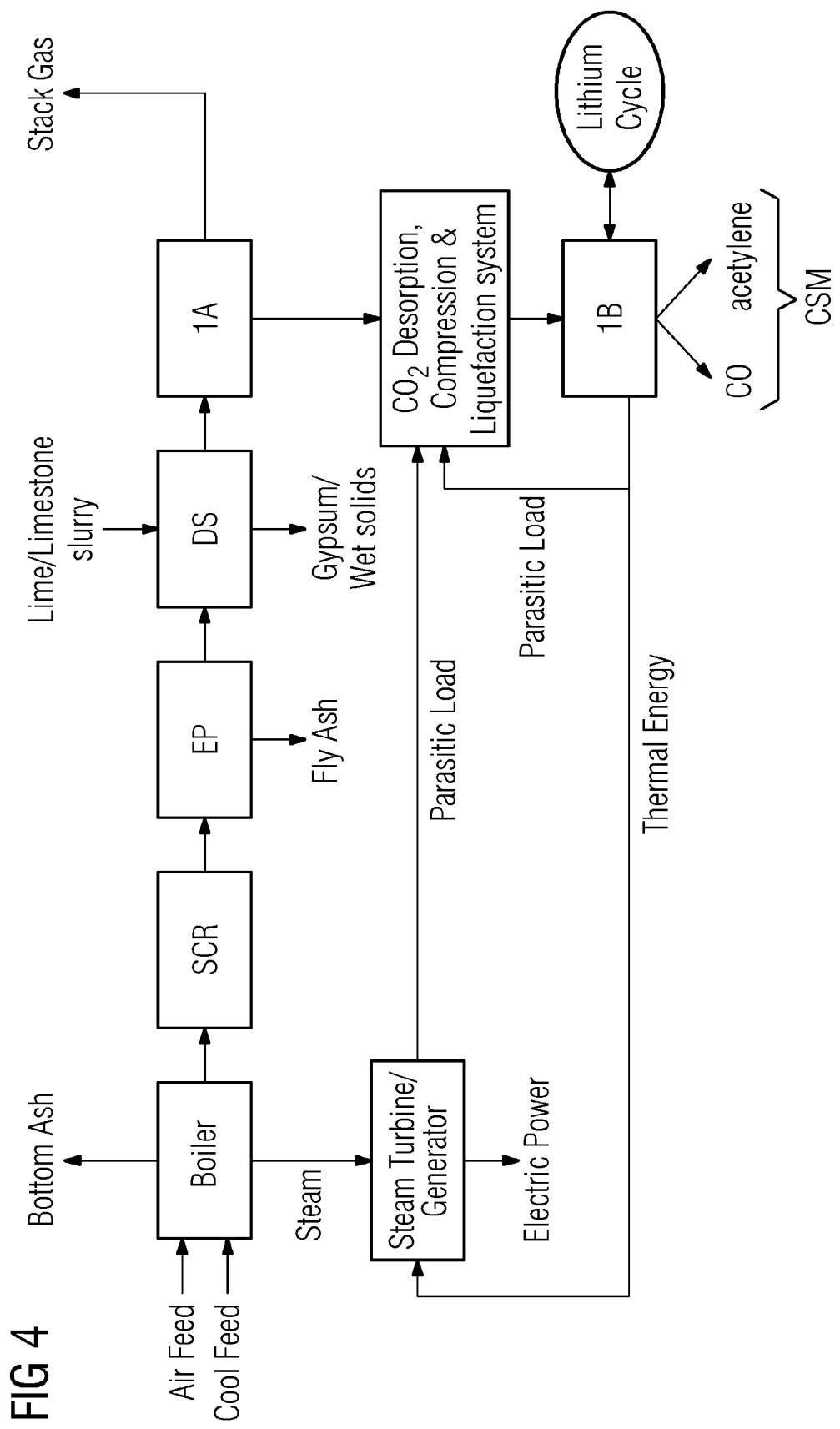
FIG. 4 shows a diagram for illustrating a post combustion carbon dioxide capture and reduction with Lithium according to a possible embodiment.

FIG. 4 shows a diagram of a post combustion carbon dioxide capture process and its reduction with lithium metal. As can be seen in FIG. 4 a boiler or combustion chamber of a combustion apparatus 2 receives an air feed A and a coal or carbon feed C. The generated heat is used to produce steam which in turn drives a steam turbine and generator such as the turbine 8 and the generator in FIGS. 1, 2. The generator 9 produces electric power. The flue gas F undergoes in the shown implementation a selective catalytic reduction SCR and passes an electrostatic precipitator EP before passing a desulfurization stage DS. In a further stage 1A a carbon dioxide $CO_2$ separation is performed by using monoethanolamine absorption as shown in FIG. 4. In a further stage a carbon dioxide desorption, compression as well as liquefaction can be performed. The isolated carbon dioxide $CO_2$ is then reduced in stage 1B with lithium Li as shown in FIG. 5. The chemical starting materials CSM produced by this burning of lithium Li within the carbon dioxide atmosphere are carbon monoxide CO as well as acetylene as shown in FIG. 4. Lithium Li can be regenerated in a lithium cycle.

In the method for industrial use of a compound comprising carbon dioxide the compound is converted in a burning step in a burning stage 1B by an electropositive metal EPM such as lithium wherein at least one burning product of the burning step is converted further in a reaction step. The chemical compound can comprise carbon dioxide and/or nitrogen.

In a preferred embodiment of the method and system lithium Li is used as the electropositive metal EPM. Lithium comprises an electro negativity of 0.98 according to the Pauling scale. Lithium Li is a substance which has the ability to react exothermically with carbon dioxide. The exothermic reaction can be used to generate thermal and electric energy. Further, lithium Li has the advantage that it can be regenerated in a closed lithium cycle as shown in FIG. 5. Lithium has a low density and is a very light material which is even lighter than water so that it can be easily transported. In a possible embodiment the regenerated lithium Li is transported as a metal in solid or liquid form. In an alternative embodiment the lithium is transported as lithium hydride in solid form. The lithium metal can be mechanically processed easily because it is relatively soft and can be cut with tools. Furthermore, lithium has one of the lowest melting points among all metals which facilitates the burning of lithium in the burning stage 1B.

The method and system for converting carbon dioxide into chemical starting materials CSM is not restricted to the use of lithium as an electropositive metal but can use other electropositive metals EPM as well such as sodium, potassium, magnesium, calcium, strontium, barium, aluminium or zinc.

The power plant that not only produces thermal and electrical energy but also chemical starting materials CSM which can be used for further chemical synthesis processes.

A power plant according to the inventors' proposal provides a closed loop conversion system 5 which receives flue gas emitted by a combustion chamber or combustion apparatus 2 of the power plant.

In an alternative embodiment the combustion chamber within the combustion apparatus 2 is provided within a mobile device such as a car or transport vehicle such as a ship. In this embodiment the loop conversion system 5 receives a flue gas from a combustion chamber 2 of a motor driving the vehicle. In a possible embodiment the closed loop conversion system 5 of FIGS. 1, 2 are integrated in the vehicle and connected to the motor of the vehicle. In this embodiment not only the carbon dioxide $CO_2$ produced by the motor is eliminated but also useful chemical starting materials CSM are produced. In a possible embodiment the chemical starting materials CSM output by the burning state 1B are sampled and stored in a container for further use. Accordingly, the inventors propose a vehicle comprising a closed loop conversion system 5 as shown in FIGS. 1, 2.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004).

The invention claimed is:

1. A method for converting carbon dioxide into chemical starting materials, the method comprising:
    isolating carbon dioxide from flue gas emitted by a combustion system, to produce an isolated carbon dioxide;
    burning an electropositive metal, in an atmosphere of the isolated carbon dioxide in an exothermic burning reaction that produces thermal energy, to reduce the isolated carbon dioxide into the chemical starting materials, wherein the electropositive metal is a lithium metal, and the burning the electropositive metal produces reaction products comprising lithium carbonate and lithium oxide;
    regenerating the lithium metal from the lithium carbonate and lithium oxide; and
    using a part of the thermal energy produced by the exothermic burning reaction of the electropositive metal with the isolated carbon dioxide to supply heat to a desorption process of a carbon dioxide capture/isolation process.

2. The method according to claim 1, wherein
    burning the electropositive metal reduces the isolated carbon dioxide to carbon monoxide and carbides, and
    the carbon monoxide is converted into carbon containing starting materials.

3. The method according to claim 1, wherein
    the method further comprises using the thermal energy to power a generator and produce electricity.

4. The method according to claim 1, wherein burning the electropositive metal comprises:
    heating the electropositive metal to provide a molten electropositive metal; and
    burning the molten electropositive metal in the atmosphere of said isolated carbon dioxide.

5. The method according to claim 1, wherein the chemical starting materials are used in further synthesis process.

6. The method according to claim 1, wherein the chemical starting materials comprise carbon monoxide and carbides.

7. The method according to claim 1, wherein
    burning the electropositive metal reduces the isolated carbon dioxide to carbon monoxide and carbides, and
    the carbides are converted into acetylene.

8. The method according to claim 1, wherein
    the lithium carbonate is converted using aqueous hydrochloride acid into lithium chloride,
    the lithium chloride is converted by electrolysis into the lithium metal.

9. The method according to claim 1, wherein
    after regeneration, the lithium metal is transported back for a subsequent burning in the atmosphere of the isolated carbon dioxide, and
    the lithium metal is transported back as a solid or liquid metal or as lithium hydride in solid form.

10. The method according to claim 1, wherein the carbon dioxide is isolated by a post combustion carbon capture system comprising a coal fired power plant (CFPP).

* * * * *